United States Patent [19]
Thompson

[11] 4,216,550
[45] Aug. 12, 1980

[54] HIP JOINT MECHANISM

[76] Inventor: Johnnie W. Thompson, Rte. 3, Box 263, Pelzer, S.C. 29669

[21] Appl. No.: 957,466

[22] Filed: Nov. 3, 1978

[51] Int. Cl.³ .............................................. A61F 1/08
[52] U.S. Cl. .............................................. 3/15; 3/21
[58] Field of Search ............................. 3/15, 16, 21, 2

[56] References Cited
U.S. PATENT DOCUMENTS

| | | | |
|---|---|---|---|
| 3,663,967 | 5/1972 | Vermillion | 3/15 |
| 3,820,169 | 6/1974 | Long et al. | 3/21 X |

FOREIGN PATENT DOCUMENTS 155917  12/1920  United Kingdom ................... 3/21

Primary Examiner—Ronald L. Frinks
Attorney, Agent, or Firm—Bailey, Dority & Flint

[57] ABSTRACT

A hip joint mechanism for adapting a leg prosthesis to a body adapter is disclosed which includes a hip hinge assembly having a hinge base and a hinge gate which pivot to accommodate pivoting of the leg prosthesis during sitting and a swivel assembly having a lock coupling providing locked and free rotational and longitudinal movement of the leg prosthesis. Means are provided for adjusting the hip joint mechanism to place the leg prosthesis in proper body and weight support alignment.

5 Claims, 4 Drawing Figures

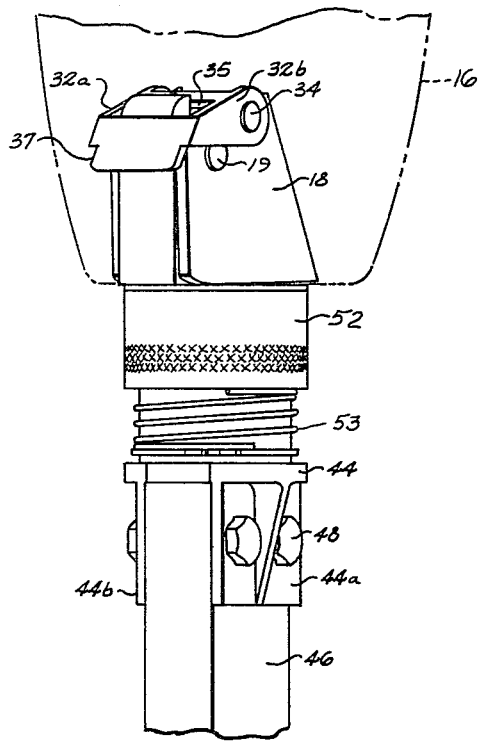
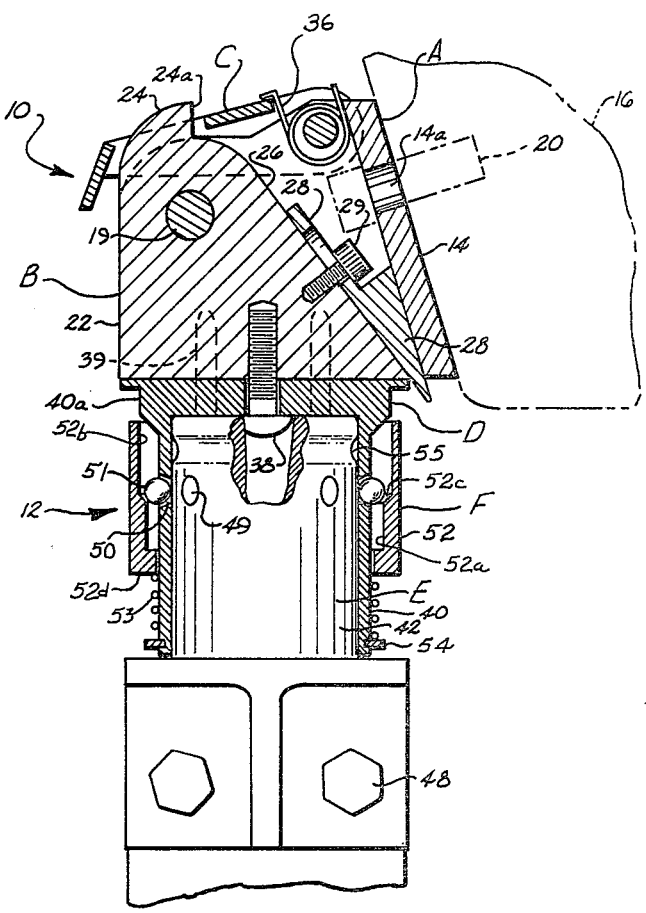
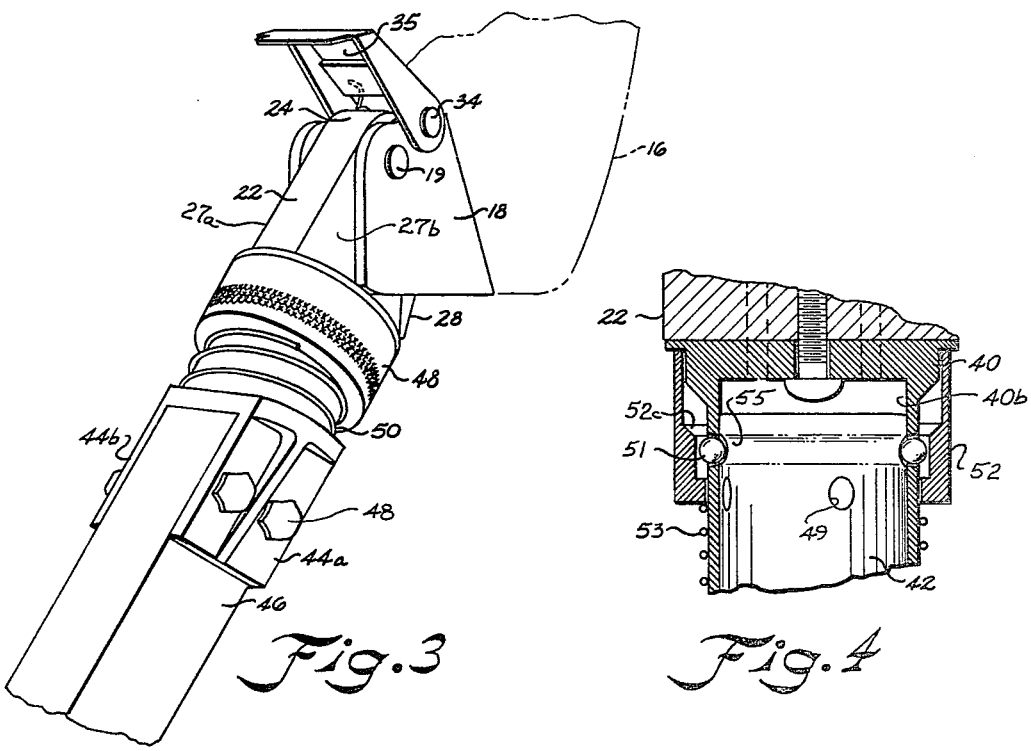
Fig. 1
Fig. 2
Fig. 3
Fig. 4

HIP JOINT MECHANISM

BACKGROUND OF THE INVENTION

Adapting an artificial leg to ones body is a problem to which considerable attention need be given for without proper adaption the leg prosthesis will not support the body weight properly nor give a natural appearance during use. The natural hip joint function is complex and simulation for adapting a leg prosthesis requires consideration not only of the hip joint functions but of the proper attachment and alignment of the leg prosthesis itself.

Accordingly, an important object of the present invention is to provide a hip joint mechanism for adapting a leg prosthesis to the body of the user which is simple yet provides the essential joint functions required for use of the leg prosthesis.

Another important object of the present invention is the provision of a hip joint mechanism which simulates the natural functions of a hip joint and which affords simple adjustment in the proper weight support and body alignment of the leg prosthesis relative to the user's body.

Still another important object of the present invention is the provision of a hip joint mechanism for adapting a leg prosthesis in which convenient and reliable locking of the different joint actions is provided.

Yet another important object of the present invention is the provision of a means for locking the different joint motions of a hip joint mechanism which are quickly releasable yet provide rigid joints for walking and weight support.

SUMMARY OF THE INVENTION

It has been found that a hip joint mechanism for adapting a leg prosthesis which assures proper alignment of the prosthesis and simulates the functions of a natural hip joint can be provided by a hip hinge assembly which includes a base hinge adapted for connection to ones body adapter and a gate hinge pivotably carried by the base hinge releasably locked therewith in a rigid configuration by means of a hinge lock. Adjustable wedging between the base and gate provides adjustment of the relative vertical alignment of the prosthesis. A swivel base is connected to the gate hinge by means which affords alignment of the prosthesis in the proper swing plane and a swivel which includes a prosthesis attachment portion is coupled to the swivel base by a lock coupling which provides locking of the prosthesis in a plurality of different rigid rotational positions and in free rotational motion while affording quick disengagement of the leg from the hip joint mechanism.

BRIEF DESCRIPTION OF THE DRAWING

The construction designed to carry out the invention will be hereinafter described, together with other features thereof.

The invention will be more readily understood from a reading of the following specification and by reference to the accompanying drawing forming a part thereof, wherein an example of the invention is shown and wherein:

FIG. 1 is a perspective view illustrating a hip joint mechanism according to the invention;

FIG. 2 is a sectional elevation with parts cut away illustrating a hip joint mechanism constructed in accordance with the invention;

FIG. 3 is a perspective view illustrating a hip joint mechanism according to the invention in a pivoted position; and FIG. 4 is a sectional elevation illustrating a swivel assembly having a lock coupling according to the invention with the swivel assembly locked to provide free rotational movement.

DESCRIPTION OF A PREFERRED EMBODIMENT

The drawing illustrates a hip joint mechanism for adapting a leg prosthesis to a body adapter of the user of the prosthesis. The hip joint mechanism includes a hip hinge assembly, designated generally at 10, having base hinge means A adapted for connection to the body adapter and a gate hinge means B pivotably connected to the base hinge means providing relative pivotal movement therebetween. A releasable hinge lock means C integrally locks the base and gate hinge means preventing relative pivotal movement therebetween affording a rigid configuration. A hip swivel assembly, designated generally at 12, includes swivel base means D connected to the gate hinge means B and a swivel means E carried by the swivel base includes means for connecting the leg prosthesis. A coupling means F is connected between the swivel and swivel base means affording relative rotational and translational movement therebetween and includes coupling lock means having a first locking position in which the swivel means may be rigidly locked in a plurality of different rotational positions relative to the swivel base means and a second locking position affording free rotational movement therebetween.

Referring now in more detail to the drawing, it can be seen that the base hinge means A includes a contoured attachment plate 14 which is adapted for connection to a conventional body adapter 16 worn by the user of the leg prosthesis. A pair of spaced-apart plates 18 extend parallel from the attachment plate 14 and accommodate a pin 19 which provides a pivot about which the hinge gate B is carried. A hole 14a drilled in the attachment plate 14 accommodates a threaded bolt 20 securing the hinge base to the body adapter, it being understood that other suitable means for attachment may also be utilized.

The hingegate B is provided in the form of a block having vertical back side 22 which projects upwardly and includes a curved top portion 24 providing a cam for interlocking with the locking means C. The cam 24 includes a flat surface 24a which terminates in a downwardly sloping surface 26 inclined to attachment plate 14. Planar side surfaces 27a and 27b are accommodated within plates 17 and 18. A means for adjusting the relative inclination between the hinge base A and the hinge gate B is provided in the form of a wedge 28 secured to the gate by a threaded screw 29 received in a closed-ended longitudinal slot 28a formed in a flat extension of the wedge 28 which provides slidable adjustment of the wedge 28 along the inclined surface 26 so as to vary the spacing and inclination between the respective base and gate hinge members.

The releasable hinge lock C is provided in the form of a latch having spaced opposed arms 32a and 32b pivotably carried on the base A by means of a pivot pin 34. A window 35 in the latch accommodates the cam portion 24 of the hinge gate to integrally lock the hinge gate and hinge base together so as to form a rigid joint of the hip hinge assembly which enables the leg movement to be controlled by the body. A spring 36 is provided for biasing the locking latch C in the locked position. A finger tab 37 is provided on the latch affording a point of leverage by one's finger to disengage the hinge latch lock allowing pivotal movement of the gate relative to the base. Such movement allows pivoting of the leg such as during sitting down from a standing position.

The hingegate B is mounted onto the swivel base D by means of a bolt 38 threaded into the gate block. Once the bolt 38 is in place, the swivel base with prosthesis attached may be rotated relative to the block of gate hinge B to align the prosthesis in the proper swing plane relative to the hip hinge assembly 10 and the user's body so that the leg swings backwards and forwards in a straight line, particularly such that the knee joint and foot portion swing straight. After alignment, additional holes 39 are bored through the swivel base into the hinge gate block and bolts are inserted to maintain the alignment and secure the mounting of the hinge gate and the swivel base.

The swivel base D is provided in the form of a hollow cylindrical sleeve 40 having a widened support base 40a and socket 40b. The swivel means E is provided in the form of a tubular insert 42 which is received within the interior of the cylindrical sleeve 40. The tubular swivel includes a leg adapter member 44 having a pair of spaced opposed mounting plates 44a and 44b which accommodate attachment to an upper support 46 of the leg prosthesis. Attachment is completed by any suitable means such as bolts 48. Accommodation can also be made for other configurations of leg supports such as round, square and the like.

The tubular swivel insert 42 includes at least one locking indenture 49 formed therein and it is preferred that four of the locking indentures be provided in the tubular insert spaced angularly apart by ninety degrees such that four different rotational locking positions are provided. Formed in the cylindrical sleeve 40 is at least one radial bore 50 and it also being preferred that four such radial bores are formed in the cylindrical sleeve corresponding in alignment with the four locking holes 49 to provide locking and rigid connection between the sleeve and tubular insert. For this purpose, locking balls 51 are received within each radial bore 50 and extend through the wall of sleeve 40 into the locking indentures 49 when it is desired to lock the swivel base D and swivel means E in any one of the four different angular positions.

An annular lock nut member 52 is provided and received about the sleeve 40 retaining the locking balls 51 and includes a reduced interior diameter portion 52a and a widened diameter portion 52b which are joined by a tapered surface 52c. The reduced diameter surface urges the locking balls into the locking indentures 49 by means of the locking nut being urged upwardly by a biasing spring 53. The biasing spring is also received about the sleeve 40 and is retained at its lower end by a locking ring 54 and at its upper end by abutment with a bottom base 52d of the locking nut. The taper 52c transfers the balls smoothly from the widened to the reduced diameter interiors automatically when the lock nut is released under force of the spring 53. The lock coupling F is in an unlocked position when the balls are in the widened interior portion 52b due to downward movement of the locknut.

The coupling F provides a first locked position with the locking balls locked in the indenture, in any of the rigid rotation positions. The first locked position provides rotation of the prosthesis to a rigid rotated position such as when exiting from and riding in an automobile. The tubular insert 42 is provided with a circumferential groove 55 adjacent the upper end thereof which provides a second locked position for the coupling F permitting free rotation between the swivel base and the swivel insert when the locking balls 51 are engaged in the groove 55 (FIG. 4). It will be noted that radial bores 50 are conical being tapered inwardly. When lock nut 52 is pulled downwardly, the locking balls 51 automatically fall outwardly from the bores releasing the balls from the indentures or groove. The balls are shown released in FIG. 2 wherein they are accommodated within the widened diameter portion of the lock nut providing an unlocked position.

Thus, it can be seen that an advantageous construction can be had for an artificial hip joint mechanism affording adaption and alignment of a leg prosthesis wherein jointed and swivel motion for sitting and like maneuvers are provided with quick and convenient releasable locking means which maintain rigid joints for walking.

While a preferred embodiment of the invention has been described using specific terms, such description is for illustrative purposes only, and it is to be understood that changes and variations may be made without departing from the spirit or scope of the following claims.

What is claimed is:

1. A hip joint mechanism for adapting a leg prosthesis to a body adapter of the user of the prosthesis comprising:

base hinge means adapted for connection to said body adapter;
gate hinge means pivotably connected to said base hinge means providing relative pivotal movement therebetween;
releasable hinge lock means integrally locking said base hinge and gate hinge means in a rigid configuration;
swivel base means connected to said gate hinge means;
swivel means carried by said swivel base means including leg adapter means adapted for connection to said leg prosthesis;
coupling means connected between said swivel and swivel base means affording relative rotational and translational movement therebetween;
said coupling means including coupling lock means having a first locked position in which said swivel means may be locked in a plurality of different rotational positions relative to said swivel base means and a second locked position affording free rotational movement therebetween;
said swivel base means including a hollow cylindrical sleeve portion and said swivel means including a tubular swivel member received within said cylindrical sleeve portion;
at least one hole formed in a wall of said cylindrical sleeve;
a locking ball received in said hole;
at least one locking recess formed in a wall of said tubular swivel member receiving said locking ball to provide a first locked position;
an annular lock nut slidably received about said cylindrical sleeve retaining said locking ball including means for biasing said locking ball in said locking position; and said biasing means of said annular lock nut including a first surface engaging said locking balls in said locking position, said annular lock nut including a second surface defining a space between said lock nut and said cylindrical sleeve in which said locking balls are retained when said annular lock nut is in an interlocking position wherein said locking balls are disengaged from said locking recess.

2. The apparatus of claim 1 including a circumferential groove formed in said wall of said tubular swivel member for receiving said locking ball providing a second locked position which affords complete free rotation between said swivel base means and said swivel means.

3. The apparatus of claim 1 including adjusting means engaging said base hinge and gate hinge means affording adjustment between the relative positions therebetween so as to place the leg prosthesis adpated thereby in proper alignment with the user's body.

4. The apparatus of claim 3 wherein said adjusting means includes a wedge means adjustable relative to said base and hinge gate means affording variation in the relative pivotal inclination therebetween.

5. The apparatus of claim 3 including cam means carried on said gate hinge means, said hinge lock means including a latch means pivotably carried by said base hinge means for engaging said cam means.

* * * * *